United States Patent [19]

Fischbarg et al.

[11] Patent Number: 4,959,355

[45] Date of Patent: Sep. 25, 1990

[54] METHOD OF INHIBITING OSMOTIC WATER FLOW

[75] Inventors: Jorge Fischbarg, New York; Larry S. Liebovitch, Long Island City; Jan P. Koniarek, Briarcliff Manor, all of N.Y.

[73] Assignee: The Trustees of Columbia University in the City of New York, New York, N.Y.

[21] Appl. No.: 25,959

[22] Filed: Mar. 16, 1987

[51] Int. Cl.$^5$ .................... A61K 31/05; A61K 31/40; A61K 31/705; A61K 31/70

[52] U.S. Cl. ........................................ 514/23; 514/25; 514/26; 514/411; 514/731; 514/733; 514/870; 536/4.1; 536/5; 536/4.4

[58] Field of Search ............. 514/25, 26, 23, 169, 514/731, 870, 909, 733; 536/4.1, 5, 18.1, 4.4

[56] References Cited

U.S. PATENT DOCUMENTS

| | | | |
|---|---|---|---|
| 3,151,108 | 9/1964 | Bosse et al. | 536/4.4 |
| 3,163,636 | 12/1964 | Wagner et al. | 536/4.4 |
| 4,101,652 | 7/1978 | Bonati | 514/26 |
| 4,470,975 | 9/1984 | Berger et al. | 536/18.5 |
| 4,665,058 | 5/1987 | Diedrich et al. | 514/25 |
| 4,684,627 | 8/1987 | LeVeen et al. | 536/18.1 |
| 4,760,135 | 7/1988 | Diedrich et al. | 536/112 |

FOREIGN PATENT DOCUMENTS 57-88122 6/1982 Japan ........................... 514/25

OTHER PUBLICATIONS

Taylor et al., Science 181:347–350, 27 Jul. 1973.
De Sousa et al., Specialia 30(2):175–177, 13 Feb. 1974.
Grosso et al., Cell & Tissue Research 188:375–388, (1978).
Fischbarg; CA79(9):51245x; Exp. Eye Res. 15(5):615–638, (1973).
Weinman et al., CA85(17):120695g; Am. J. Physiol. 231(3):777–780, (1976).
Dorland; The American Illustrated Medical Dictionary, p. 421 (1981), W. B. Saunders Co., Philadelphia.

*Primary Examiner*—Ronald W. Griffin
*Assistant Examiner*—Nancy S. Carson
*Attorney, Agent, or Firm*—John P. White

[57] ABSTRACT

This invention provides a method of inhibiting osmotic water flow across mammalian cell membranes which involves contacting the water channels of the cell membranes with an effective amount of a glucose transport blocker or of digitonin so as to inhibit osmotic water flow across the membranes.

Additionally, this invention provides a method of treating a subject afflicted with a condition associated with abnormal osmotic water flow across cell membranes which comprises administering to the subject an effective amount of a glucose transport blocker or of digitonin so as to contact the water channels of the subject's cell membranes and inhibit osmotic water flow across the membranes.

9 Claims, 1 Drawing Sheet

METHOD OF INHIBITING OSMOTIC WATER FLOW

The invention described herein was made with government support under grant numbers EY01080, EY06178 and EY06234 from the National Institutes of Health, United States Department of Health and Human Services. The U.S. Government has certain rights in this invention.

BACKGROUND OF THE INVENTION

Throughout this application various publications are referenced by numbers within parentheses. Full citations for these publications may be found at the end of the specification immediately preceding the claims. The disclosures of these publications, in their entireties, are hereby incorporated by reference into this application in order to more fully describe the state of the art to which this invention pertains.

Corneal endothelial fluid transport: This invention originates from prior studies on water relations in the cornea of the eye. This organ is kept transparent by the activity of its posterior epithelial monocellular cell layer, the endothelium, which displays a high osmotic permeability [1,2] and transports significant amounts of electrolytes and water [3,4] across itself. In the course of the studies disclosed herein on the basic mechanism of this fluid transport [4], recent evidence has [2] led us to conclude that the transendothelial transport of water most probably takes place across the cell membranes, just as it appears to do in other water-transporting epithelia such as the gall bladder [5].

The route for water permeation through cell membranes: In order to explain fluid transport fully, one would need to know the basic mechanism of water movements through cells and tissues. Yet, although water movements across cell membranes are a most ubiquitous and important feature of living processes, the precise route for it remains unclear. Thus, it has been variously suggested (6) that water simply traverses the lipid bilayer in most membranes except for those most permeable, where it would in addition traverse a water pore (7), also called a water channel (8), which would constitute a polar route across the lipid bilayer.

Studies of this latter route in human erythrocyte membranes had led to the suggestion (9,10) that the transmembrane protein (band 3) containing the anion channel (11, 12) is the route of the water transport. However, later evidence has cast doubts on such suggestion. For example, 5,5-dithiobis (2-nitrobenzoate), (DTNB), which is a good blocker of and marker for the anion channel in red blood cells, has been variously reported to block osmotic water flow by 60% (13) and not to affect water permeability (14). This discrepancy is important, since the observed inhibitory effect of DTNB on osmotic flow was central for the argument that the anion channel is the water permeation route (10). More recent evidence has pointed to either the anion channel or the glucose transporter or both (bands 3.0 and 4.5) as the water permeation site. (15, 16); still more definite identification could not be done for lack of evidence that any specific inhibitor of those proteins would block water transport.

The glucose transporter as water channel: Given this background, reexamination has been made of the effect on osmotic water flow of blockers of sulfhydryl groups and of both anion and glucose permeation. Two of the approaches utilized appear to be novel for this area of work:

(a) water flow was measured across an epithelial preparation (the corneal endothelium) instead of red blood cells, and,
(b) rather than determining osmotically-induced cell volume changes (as done classically with red blood cells), the rate of water flow as a function of time was monitored continuously.

While some prior results obtained with erythrocytes were confirmed, a crucial difference also was found, namely, that in the preparation all glucose transport inhibitors blocked osmotic water flow. The conclusion that emerged from these experiments is consistent with the hypothesis that both water and glucose traverse cell membranes through the same channel-like pathway, that is, through the protein identified as the glucose transporter (band 4.5). An account of some of these early findings has appeared in Abstract form [17].

SUMMARY OF THE INVENTION

This invention provides a method of inhibiting osmotic water flow across mammalian cell membranes. The method comprises contacting the water channels of cell membranes with an effective amount of a glucose transport blocker so as to inhibit osmotic water flow across the membranes.

This invention also provides a method of inhibiting osmotic water flow across mammalian cell membranes which comprises contacting the water channels of cell membranes with an effective amount of digitonin so as to inhibit osmotic water flow across the membranes.

Moreover, this invention provides a method of treating a subject afflicted with a condition associated with abnormal osmotic water flow across cell membranes. The method comprises administering to the subject an effective amount of a glucose transport blocker so as to contact the water channels of the subject's cell membranes and inhibit osmotic water flow across the membranes.

Finally, the invention provides a method of treating a subject afflicted with a condition associated with abnormal osmotic water flow across cell membranes which comprises administering to the subject an effective amount of digitonin so as to contact the water channels of the subject's cell membranes and inhibit osmotic water flow across the membranes.

Figure 1:
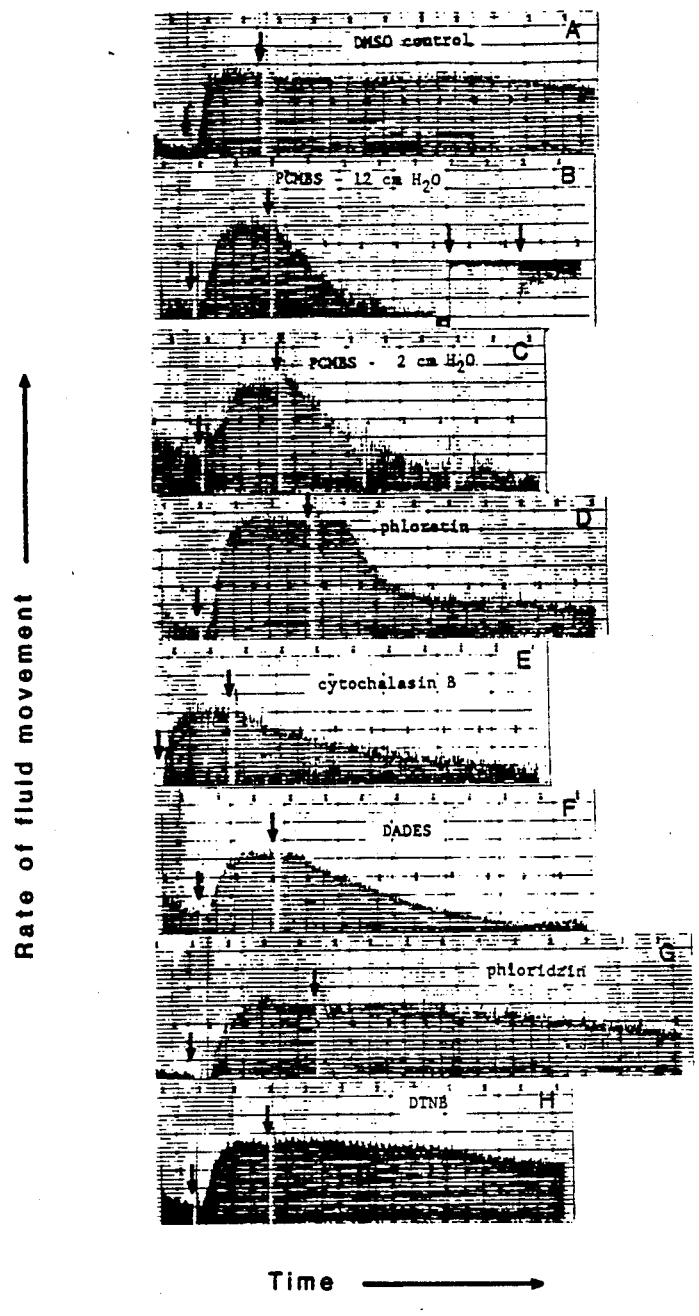
FIG. 1. Transendothelial water flow as a function of time in photographs of the original recorder charts. Scale of ordinate: 1 large division=100 nl/min; scale of abscissa: 1 division=15 min. The positive direction in the ordinate (positive flow) signifies movement of water from the stromal (basal) side to the aqueous (apical) side. Unless specified, a hydrostatic pressure head of 12 cm $H_2O$ was applied to the aqueous side. Going from left to right in the panels, fluid transport normally ensued, after which the first arrow marks the establishment of an osmotic gradient of 200 mosM by substituting a hypertonic solution on the aqueous side. Unless specified, the osmotic agent was DMSO. The second arrow marks the second manipulation, usually the addition of a test compound (also by substitution of the solution on the aqueous side).

(A): Expt. No. 34; control experiment; at the second arrow, the solution on the aqueous side (BSG) was completely replaced by fresh BSG.

(B): Expt. No. 82; test compound 2 mmol/l p-chloromercuribenzene sulfonate (PCMBS); after some 4 hours, when the flow reversed its direction, the baseline of the recording was repositioned (third arrow). At the fourth arrow, the hydrostatic pressure head was increased from 12 to 18 cm $H_2O$, and an increased leak ensued.

(C) Expt. No. 81; test compound: 2 mmol/l PCMBS; hydrostatic pressure head: 2cm $H_2O$.

(D) Exp. No. 76; osmotic agent: sucrose; test compound: 2 mM phloretin.

(E) Expt. No. 48; test compound: 20 μg/ml cytochalasin B.

(F) Expt. No. 58; test compound: 0.1 mM 3,3'-diallyldiethylstilbestrol (DADES).

(G) Expt. No. 30; test compound: 2 mM phloridrin.

(H) Expt. No. 67; test compound: 2 mM DTNB.

DETAILED DESCRIPTION OF THE INVENTION

This invention provides a method of inhibiting osmotic water flow across mammalian cell membranes. The method comprises contacting the water channels of the cell membranes with an effective amount of a glucose transport blocker so as to inhibit osmotic water flow across the membranes.

Although any glucose transport blocker may be employed in the practice of the method, the following glucose transport blockers have been employed phloridzin, phloretin, diallyldiethylstilbestrol, cytochalasin B and ethylidene-D-glucose. Of these, diallyldiethylstilbestrol, cytochalasin B, and ethylidene-D-glucose are particularly useful.

This invention also provides a method of inhibiting osmotic water flow across cell membranes which comprises contacting the water channels of the cell membranes with an effective amount of digitonin so as to inhibit osmotic water flow across the membranes.

Moreover, this invention provides a method of treating a subject afflicted with a condition associated with abnormal, e.g. excessive osmotic water flow across cell membranes. The method comprises administering to the subject an effective amount of a glucose transport blocker so as to contact the water channels of the cell membranes and inhibit osmotic water flow across the membranes.

This method is particularly suitable for use in the treatment of a subject afflicted with the following conditions: diuresis, kidney dysfunction, obesity, edema, e.g. edema of the lung or brain, neurosis or phychosis.

Although any glucose transport blocker may be employed in the treatment of a subject afflicted with a condition associated with abnormal osmotic water flow across cell membranes, the following glucose transport blockers have been employed: phloridzin, phloretin, diallyldiethylstibestrol, cytochalasin B and ethylidene-D-glucose. Of these, diallyldiethylstilbestrol, cytochalasin B, and ethylidene-D-glucose are presently preferred.

Finally, the invention provides a method of treating a subject afflicted with a condition associated with abnormal, particularly excessive osmotic water flow across cell membranes. The method comprises administering to the subject an effective amount of digitonin so as to contact the water channels of the cell membranes and inhibit osmotic water flow across the membranes.

This method is particularly suitable for use in the treatment of a subject afflicted with the following conditions: diuresis, kidney dysfunction, obesity, edema, e.g. edema of the lung or brain, neurosis or phychosis.

EXPERIMENTAL RESULTS

Method

The isolated rabbit corneal endothelium was mounted in a chamber so as to separate two compartments filled with the appropriate experimental solutions. The water flow across it was measured as previously (18) described (except that an infrared sensor was now used to detect water level). The solution on the aqueous side was bubbled with a 95% air/5% $CO_2$ mixture saturated with water vapor. The hydrostatic pressure difference across the tissue ($P_{aqueous} - P_{stroma}$) was 12 cm $H_2O$, and the temperature was kept at 36.820 C. Both sides of the preparation were bathed with basal salts plus 6.9 mM glucose (BSG solution). After mounting, the endothelial preparation typically developed its characteristic spontaneous rate of fluid transport towards the aqueous side (6 to 10 μl/h/cm²). After monitoring this for about 90 min, a relatively large osmotic flow (12 to 20 μL/h/cm₂ total) was induced by making the aqueous side hypertonic by 200 mosmol/l above BSG tonicity. The compound utilized as osmotic agents were either dimethyl sulfoxide (DMSO), propionamide, sucrose or glucose. After attaining a steady osmotic flow, a blocker was added while retaining the osmotic gradient. The blockers used were p-chloromercuribenzene sulfonate (PCMBS), 5,5'-dithiobis-(2-nitrobenzoate) (DTNB), 4,4'diisothiocyanatostilbene-2,2-disulfonate (DIDS), phloridzin, phloretin, cytochalasin B and dihydrocytochalasin B (all obtained from Sigma, St. Louis, Mo.) 4,6-0-ethylidene-D-glucose (from Aldrich, Milwaukee, Wis.), and 3,3'diallyldiethylstilbestrol (DADES) (prepared by Lee's Bio-Organic Labs., Marcus Hook, Pa.).

Results

Sulfhydryl blocker: As in studies in human erythrocytes (19, 20, 21), the osmotic flow was inhibited by the sulfhydryl blocker PCMBS (FIG. 1B, 1C and Table I). After adding the inhibitor, there was a short delay, and then the rate of flow decreased exponentially. The same form of time dependence was seen with the other

TABLE I

EFFECTS OF BLOCKERS ON TRANSENDOTHELIAL OSMOTIC FLOWS

| Osmotic agent (mol/l) and blocker (mmol/l)$^a$ | Expt. No. | Osmotic flow (nl/min) | Delay (min) (Av. ± S.E.) | Rate of inhibition or decline (%/min) (Av. ± S.E.) |
|---|---|---|---|---|
| DMSO (0.2) | 1 | 475 | 15 | 0.51 |
| PCMBS (0.5) | 21 | 490 | 22 | 1.10 |
| | 22 | 510 | 15 | 0.93 |
| | 26 | 375 | 78 | 0.57 |
| | | | 33 ± 13 | 0.78 ± 0.12 |
| DMSO (0.2) | 20 | 600 | 13 | 1.30 |
| PCMBS (1.0) | 23 | 545 | 11 | 1.19 |
| | 25 | 300 | 18 | 1.52 |
| | | | 14 ± 2 | 1.34 ± 0.08 |
| DMSO (0.2) | 19 | 440 | 11 | 1.16 |
| PCMBS (2.0) | 24 | 290 | 9 | 1.59 |
| | 82 | 404 | 6 | 1.67 |
| | 83 | 305 | 3 | 1.75 |
| | | | 7 ± 2 | 1.54 ± 0.11 |
| DMSO (0.2) | 79 | 3.85 | 16 | 1.61 |
| PCMBS (2.0) | 80 | 250 | 16 | 2.50 |
| ΔP-2 cm $H_2O$ | 81 | 400 | 12 | 1.52 |
| | | | 15 ± 1 | 1.88 ± 0.26 |
| DMSO (0.2) | 30 | 375 | 108 | 0.48 |

TABLE I-continued
EFFECTS OF BLOCKERS ON TRANSENDOTHELIAL OSMOTIC FLOWS

| Osmotic agent (mol/l) and blocker (mmol/l)[a] | Expt. No. | Osmotic flow (nl/min) | Delay (min) (Av. ± S.E.) | Rate of inhibition or decline (%/min) (Av. ± S.E.) |
|---|---|---|---|---|
| Phloridzin (2.0) | 64 | 225 | 177 | 0.37 |
|  | 65 | 395 | 150 | 0.23 |
|  | 68 | 325 | 119 | 0.35 |
|  | 69 | 370 | 187 | 0.66 |
|  |  |  | 148 ± 14 | 0.42 ± 0.06 |
| DMSO (0.2) | 31 | 345 | 8 | 0.39 |
| Phloretin (2.0) | 32 | 315 | 9 | 0.47 |
|  | 36 | 305 | 12 | 0.80 |
|  | 37 | 410 | 15 | 1.85 |
|  | 38 | 350 | 12 | 0.78 |
|  |  |  | 11 ± 1 | 0.86 ± 0.23 |
| Sucrose (0.2) | 73 | 555 | 33 | 1.85 |
| Phloretin (2.0) | 74 | 600 | 40 | 1.61 |
|  | 75 | 690 | 47 | 1.25 |
|  | 76 | 575 | 30 | 2.00 |
|  |  |  | 38 ± 3 | 1.68 ± 0.14 |
| Propionamide (0.1) | 43 | 125 | 27 | 0.85 |
|  | 44 | 175 | 24 | 0.95 |
| Phloretin (2.0) | 46 | 105 | 33 | 0.71 |
|  | 70 | 120 | 26 | 0.61 |
|  |  |  | 28 ± 2 | 0.78 ± 0.06 |
| DMSO (0.2) | 48 | 420 | 11 | 0.86 |
| Cytochalasin B (20 µg/ml) | 49 | 330 | 10 | 0.60 |
|  | 50 | 385 | 8 | 1.96 |
|  | 72 | 400 | 118 | 0.33 |
|  | 92 | 300 | 54 | 0.79 |
|  |  |  | 40 ± 19 | 0.91 ± 0.25 |
| DMSO (0.2) | 56 | 357 | 51 | 0.66 |
| DADES (0.1) | 57 | 315 | 34 | 0.99 |
|  | 58 | 305 | 19 | 0.79 |
|  | 71 | 340 | 165 | 1.52 |
|  |  |  | 67 ± 29 | 0.99 ± 0.16 |
| D-Glucose (0.2) | 97 | 315 | 42 | 0.65 |
|  | 98 | 505 | 27 | 0.83 |
| Ethylidene-D-glucose (200) (200) | 99 | 375 | 60 | 1.39 |
|  | 100 | 420 | 39 | 1.14 |
|  | 101 | 380 | 32 | 1.64 |
|  | 102 | 395 | 33 | 1.02 |
|  |  |  | 39 ± 4 | 1.11 ± 0.14 |
| DMSO (0.2) | 27 | 300 | 161 | 0.35 |
| DTNB (2.0) | 28 | 430 | 64 | 0.20 |
|  | 66 | 225 | 192 | 0.30 |
|  | 67 | 340 | 75 | 0.15 |
|  |  |  | 123 ± 27 | 0.25 ± 0.04 |
| DMSO (0.2) | 88 | 250 | 52 | 0.19 |
| DIDS (0.050) | 89 | 400 | 184 | 0.28 |
|  | 90 | 300 | 75 | 0.28 |
|  | 91 | 375 | 143 | 0.23 |
|  |  |  | 114 ± 26 | 0.25 ± 0.02 |
| DMSO (0.2) 1% ethanol (control) | 59 | 370 | 13 | 0.14 |
|  | 60 | 330 | 150 | 0.25 |
|  | 86 | 250 | 68 | 0.50 |
|  | 87 | 325 | 205 | 0.42 |
|  |  |  | 109 ± 37 | 0.33 ± 0.07 |
| DMSO (0.2) no blocker (control) | 34 | 385 | 205 | 0.19 |
|  | 35 | 435 | 170 | 0.31 |
|  | 84 | 300 | 272 | 0.30 |
|  | 85 | 205 | 300 | 0.29 |
|  |  |  | 237 ± 26 | 0.27 ± 0.02 |

[a]Except where noted.

inhibitors (FIG. 1). Thus, the initial rates of inhibition were determined (Table I) from the initial slopes of the exponentials in each case. For comparison, Table I also includes results obtained in control experiments done by imposing an osmotic gradient without the subsequent use of inhibitors. As the example in FIG. 1A shows, in such experiments the osmotic flow remained constant for a relatively long period, and then it declined very slowly.

Anion channel blockers: Also studied was the effect of the anion channel blockers DTNB and DIDS on osmotic flow. The results obtained were consistent with those of Benga et al. (14) for both blockers, in spite of the difference in methods and preparation. Benga et al. measured human erythrocyte $H_2O$ diffusional permeability. The experiments disclosed herein demonstrate that DTNB (2 µmM) had only a modest effect, which was not statistically significant (FIG. 1H and Table I). Similarly, DIDS (50 M) had no significant effect on osmotic flow (Table I).

Inhibitors of the Glucose Transporter: The carrier for facilitated diffusion of glucose or glucose transporter (22, 28) is a good candidate for the role of a water channel It is a well studied membrane protein; recently, the transporters of two human cells have been sequenced (22). It traverses the membrane entirely, it is present in most if not all animal cells (23), and where the number of molecules per cell has been estimated as in human red blood cells (24, 25), it is present in the relatively large numbers that would be necessary to have it account for significant water permeation. In addition, recent work by Benga and his co-workers (15, 16) strongly suggests that the water channels could only be either the anion channel or the glucose transporter or both. However, counter to this idea, previous work from several other laboratories using human red blood cells (19, 20, 14, 26) has shown no effect on water permeation by phloretin, a well-known enzymatic inhibitor (27) which is particularly effective in blocking the facilitated diffusion of glucose across the membranes of several types of cells (28, 29). In fact, to date, there is no evidence that any specific inhibitor of the glucose transporter (or of the anion channel) will block water transport and hence, precise identification of the water route has not been possible so far.

Given this background, the results disclosed herein were somewhat surprising; demonstrating that phloretin (2 mmol/l) clearly inhibited osmotic flow (Table I and FIG. 1D). Furthermore, this inhibition by phloretin took place with either DMSO, propionamide, or sucrose as osmotic agents (Table I). Phloridzin (2 mmol/l) also inhibited water flow, although to a much smaller extent (Table I and FIG. 1G). This parallels the relative blocking effects of these two compounds on facilitated diffusion of glucose in some types of cells (29).

Several other glucose transport inhibitors subsequently were utilized. Tested compounds included DADES, a compound in a group known to include some of the most potent blockers of facilitated diffusion of glucose (24, 26; 50% inhibition is reached with less than 1 µM with this class of blockers). Its pronounced inhibitory effect on osmotic flow is shown in FIG. 1F and Table I. In keeping with this pattern, cytochalasin B, another known blocker (31, 32) of facilitated diffusion, also markedly inhibited osmotic flow, as shown on FIG. 1E and Table I. This last result was firmed up by four control experiments done with dihydrocytochalasin B, which acts on cell mobility and morphology but does not affect the glucose transporter (33). Dihydrocytochalasin B did not affect the osmotic flow. Lastly, ethylidene-D-glucose, which is also known to inhibit glucose transport (34, 35, 36), was tested and it was verified that it also blocked the osmotic flow (Table I).

The rates of inhibition in Table I give an idea of the relative potency of each of the inhibitors at the concentrations utilized. To be noted, cytochalasin B and DADES inhibit osmotic flow at lower concentrations than the other inhibitors, which is in line with their known behavior towards the glucose transporter. The rate of inhibition with phloretin was larger when sucrose was the osmotic agent than when either DMSO or propionamide were used. This may indicate some competition between phloretin, DMSO and propionamide for the blocking site. Still, the inhibitory effects were typically very large; thus, with the more potent inhibitors, after some 1-2 h the flow typically had fallen by 75 to 90% with respect to that during the control period (FIG. 1). On the other hand, experiments performed with the osmotic agents alone (such as DMSO) or in addition to the ethanol used as vehicle for DADES (Phloretin, which is insoluble in water at ambient temperature, dissolved at the 36.8° C. utilized here.) showed that the osmotic flow remained nearly constant for quite a long period of time (FIG. 1A, Table I).

Control experiments: Since the experiments must be carried out with a hydrostatic pressure gradient ($\Delta P$) applied to the aqueous side (2b), it might be argued that the decrease in positive flow observed with the different blockers (FIG. 1) might be due at least partially to an increased passive fluid leak across the paracellular pathway driven by the standard 12 cm $H_2O$ $\Delta P$ utilized. However, at least three different lines of evidence contradict this possibility.

(1) The actual rate of leak driven by $\Delta P$ was determined after the osmotic flow had been inhibited and was found to be relatively small. An example is shown in FIG. 1B.

(2) The tissue was exposed to an osmotic gradient, and then to Ca-free medium while maintaining the osmotic gradient. Since the apical intercellular junctions are known to open under these conditions (37), the positive flow decreased, reflecting an increased leak. However, the residual positive flow was still inhibited by the subsequent addition of 2 mM PCMBS.

(3) Perhaps most definitively of all, when these experiments were done with a reduced hydrostatic pressure gradient of only 2 cm $H_2O$, the inhibitory effects observed (Table I and FIG. 1C) were the same as with the larger $\Delta P$.

Digitonin: It also has been unexpectedly noted, using substantially the same experimental procedures disclosed herein, that digitonin, although not a glucose transport blocker, and escin, which is presently not known to be a glucose transport blocker, will inhibit osmotic water flow across cell membranes.

Discussion

Significance of the present findings: The idea that the glucose transporter might be the 'pore' or channel sought for water permeation is not new in itself. It appeared in, among others, papers by Macey and Farmer [19], Owens and Solomon [26] and Benga et al. [14], but since in those cases phloretin was found not to affect water osmosis (or diffusion) in human erythrocytes, the notion remained questionable. It was also mentioned in a similar light in a recent paper by Solomon et al. [10] and in a review by Macey [8]. Very recently, however, the view acquired new viability with the results of Benga and his coworkers [15, 16]. From the patterns of PCMBS binding to cell proteins and water diffusion inhibition, they concluded that either or both the anion channel or the glucose transporter could be associated with water channels, although they cautioned that 'to date, there is no evidence that a specific inhibitor of one of these processes will inhibit water transport'.

The experiments disclosed herein point squarely to the glucose transporter as the site of water permeation. To summarize, the experiments indicate, apparently for the first time, that several known blockers of facilitated diffusion of glucose, namely, phloridzin, phloretin, DADES, cytochalasin B, and ethylidene-D-glucose, all inhibit transendothelial osmotic flow. The degree of specificity of each one of them separately for the glucose transporter can, of course, be argued about; for instance, phloretin and phloridzin also block $Cl^-$ (38) and $SO_4^{2-}$ (49) permeation erythrocytes. However, the relevance of such observations is dubious, since DIDS, which blocks the anion channel in erythrocytes (8), did not affect the osmotic flow in the experiments described herein. Certainly, no such reservations can be voiced for two other inhibitors utilized, DADES and ethylidene-D-glucose, which seem quite specific for the glucose transporter (28, 30 for DADES; 34-36 for ethylidene-D-glucose). As for cytochalasin B, a popular and potent blocker of the glucose transporter, the possibility of indirect effects via its parallel effect on actin filaments was discarded by verifying that dihydrocytochalasin B, which has the same morphological effects as its parent compound but does not affect glucose transport, did not block the osmotic flow.

For emphasis, it may be noted that "success", defined as blockage by glucose transport inhibitors and non-blockage by non-glucose transport inhibitors, was achieved all 55 times in the 55 pertinent experiments in Table I. Assigning an arbitrary probability of 0.5 to such success by chance, the probability that the results herein disclosed were due to chance would be $2.8 \times 10^{-17}$, that is to say, zero.

Estimates of the number of permeation sites in corneal endothelium: The endothelium is the site of a sizable glucose facilitated diffusion mechanism (3), which is a requisite for the present reasoning. The number of sites or interest can be estimated in two ways: (a) from glucose flux measurements, and (b) from osmotic permeability values. In the first case, using a published value of $5.56 \times 10^{-6}$ mM/cm$^2$/min for the $V_{max}$ of methyl-D-glucose transport mechanism (40), a transfer rate of $1.75 \times 10^8$ molecules/cell/sec. is obtained. Using an estimate for the turnover of 1000 molecules/site/sec (derived from erythrocyte data), the site density is $1.8 \times 10^5$ sites/cell. In the second case, a hydraulic conductance of $8.2 \times 10^{-13}$ cm/sec/site ($\times 1$ cm$^2$ of area) was calculated based on Poiseuille's law. Given an apical hydraulic conductance of 0.14 cm/sec (2), a value of $5.3 \times 10^5$ sites/cell was reached, which agrees with the order of magnitude of the other estimate above. Granted that these order-of-magnitude estimates are not to be overemphasized, the agreement nevertheless appears interesting and is consistent with the present reasoning.

Present and prior results: Discrepancies between prior and present results exist, but can be accounted for. The difference between the effects of phloretin on human erythrocytes and on rabbit corneal endothelium may be due to a difference in tissue properties, or in the experimental conditions. The slow time course for the inhibition herein observed is at variance with inhibitory effects on the transporter, which are much faster. However, under the experimental conditions, the large concomitant osmotic flow, the presence of ambient glucose, and cellular activity, all (especially the first) might interfere with inhibition.

Prior implicit evidence for water permeation thorough the glucose channel: It seems interesting that, although conclusions as definite as the present ones have not apparently been drawn, evidence consistent with this notion has appeared in the literature. Some examples:

(1) Blocking effects of SH reagents: Inhibition by such agents as PCMBS on both glucose facilitated diffusion [29] and osmotic water flow [19-21] are well known, but a firm connection between these two lines of findings apparently has not been made until now.

(2) Water molecules permeating together with sugars: Arguments have been advanced for the presence of randomized water molecules inside a polar channel through which sugars are transported [14].

(3) Molecular radii: Using CPK models and Stokes law, others have estimated the molecular radii of glucose and sucrose. The averages of the published values are 0.40 nm and 0.49 nm, respectively. Turning now to the glucose transporter, the membrane-spanning domains in the model suggested by Mueckler et al. [22] can be arranged so as to generate a structure with a central channel. Since the glucose transporter exhibits great specificity for D-glucose and other monosaccharides but excludes disaccharides [28, 29, 42], it may be assumed that the transporter channel radius lies somewhere disaccharide (0.40 to 0.49 nm). Such channel would admit the water molecules radius (approx. 0.15 nm) [43] readily. Conformation changes in the transporter would not change this basic picture, since at some point the channel would have to admit monosaccharides.

(4) Solomon's hypothesis and the results disclosed herein: As another interesting aspect of this reasoning, the range of 0.40-0.49 nm theorized just above for the radius of the glucose transporter channel brackets the 0.42-0.46 nm range for the radius of equivalent water pores calculated by Solomon and his co-workers [7, 44]. There has been considerable discussion [45-49] of the validity of Solomon's and similar calculations. Such discussion may not be fueled by the fact that, from the arguments above, so far, our own results appear consistent with their thesis. At the same time, as mentioned above, the present results do not support the more recent view (as expounded in Solomon et al. [10]) that the band 3 anion channel is the predominant site of water permeation. True, there is some residual osmotic flow after treatment with some of the glucose transporter blockers and DTNB had a slight but not statistically significant inhibitory effect, so that minor alternative pathways for water permeation such as the anion channel cannot be excluded.

(5) Polar transmembrane route: Molecular models of water and glucose [50] suggest that the 0 and H atoms in the glucopyranose form may interact with the glucose transporter channel sites just as water might. In fact, it has been suggested [22] that hydroxyl and amide side chains may line the transporter transmembrane channel and provide a polar and uncharged environment. Obviously such an environment would be quite suitable for the binding and migration of water molecules.

(6) Erythrocyte osmotic permeability and the hydrodynamic pore theory: It does not seem clear at present whether the permeation of water through transmembrane channels can be described in terms of the hydrodynamics of solvent flow across right cylinders of uniform cross section (see, for example, Ref. 7). Galey and Brahm [49] have pointed out that such assumption leads to inconsistencies when attempting to account for both osmotic and diffusional water permeation across erythrocyte membranes; they favor the view that such permeation takes place in single-file mode. Still, given the current results, the possibility that water may indeed be traversing an open channel some 0.45 nm in radius is too appealing to be discarded out of hand. Strictly for argument, then, it will be assumed that such is the case for human erythrocytes. The present studies verify that, curiously, the osmotic permeability calculated for the putative channels in band 4.5 results in values of the order of published ones. Assuming cylindrical channels 0.45 nm in radius and 0.40 nm long, and using values of $1.3 \cdot 10^5$ [24] to $5.5 \cdot 10^5$ [25] for the total number NT of glucose transporter molecules per cell, and a cell area of $1.35 \cdot 10^{-6}$ cm$^2$ [51, 52, 10], the erythrocyte's hydraulic conductance based on Poiseuille's law [53] would be $$L_p RT/V_w = [(r^4)/81)] \times [NT/A_{cell}] = 790 \text{ to } 3500 \text{ } \mu m/s$$

while representative published values are 110-340 m/s [54]. Thus RBS osmotic permeability could be comfortably accounted for by the minimum value calculated for its glucose transporters. It is presumed that these issues are bound to receive renewed attention.

Conclusion: This invention includes evidence only for osmotic flows. For more detailed support of this hypothesis one might want to have more extensive information on the glucose transporter characteristics than there is in the literature for this tissue. Yet, barring an exceedingly implausible coincidence, the mere fact that all glucose transport inhibitors tested so far do inhibit osmotic flow in the preparation strongly suggests that water and glucose traverse the same path across these cell membranes. This in turn raises the tantalizing possibility that future work might show that the glucose transporter channels might constitute the main route for water permeation across the membranes of all animal cells.

REFERENCES

1. Klyce, S.D. and Wong, R.K.S., J. Physiol. 266, 777 (1977).
2. Pischberg, J. and . Montoreano, R., Biochim, Biophys. Acta 690, 207 (1982).
3. Maurice, D.M., in "The Eye", H. Davson, Ed., Ch. 1, (Acad. Press, N.Y., 1983);
4. Fischberg, J., Hernandez, J., Liebovitch, L.S., Korniarek, J.P., Curr. Eye Res. 5, 351 (1985).
5. Persson, B.-E. and Spring, K.R., J. Gen. Physiol. 79, 481 (1982).
6. Finkelstein, A., in "Current Topics in Membranes and Transport", Stein W. and Bronner, H., Eds., p. 295 (Acad. Press, N.Y., 1984).
7. Goldstein, D.A. and Solomon, A.K., J. Gen. Physiol. 44, 1 (1960).
8. Macey, R.I., Am. J. Physiol. 246 (Cell Physiol. 15), C195 (1984).
9. Brown, A.P. Feinstein, M.B., Sha'afi, R.I., Nature 254, 523 (1975).
10. Solomon, A.K., Chasan, B., Dix, J.A., Lukacovic, M.F., Toon, M.R., Verkman, A.S., Ann, N.Y. Acad Sci. 414, 97 (1983).
11. Fairbanks, G., Steck, T.L., Wallach, D.F.H., Biochem. 10, 2606 (1971).

12. Cabantchik, Z.I., Knauf, P.A., Rothstein, A., Biochim. Biophys. Acta 515, 239 (1978).
13. Naccache, P. and Sha'afi, R.I., J. Cell Physiol. 83, 449 (1974).
14. Benga, G., Pop, V.I., Propescu, O., Ionescu, M., Mihele, V., J. Memb. Biol. 76, 129 (1983).
15. Benga, G., Popescu, O., Pop, V.I., Biochem. 25, 1535 (1986).
16. Benga, G., Popescu, O., Borza, V., Pop, V.I., Muresan, A., Mocsy, I., Brain, A., Wrigglesworth, J.M., Europ. J. Cell Biol. 41, 252 (1986).
17. Fischbarg, J., Liebovitch, L.S., Koniarek, J.P., ARVO Abstrs., Suppl. to Invest. Ophthal., 27, N83, p.84 (1986).
18. Fischbarg, J., Lim, J.J., Bourguet, J., J. Memb. Biol. 35, 95 (1977).
19. Macey, R.I. and Farmer, R.E.L., Biochim. Biophys. Acta 211, 104 (1970).
20. Macey, R.I., Karan, D.M., Farmer, R.E.L., in "Biomembranes", Kreuzer, F. and Slegers, J.F.G., Eds., p. 331 (Plenum Press, New York, 1972).
21. Sha'ali, R.I. and Feinstein, M.B., in "Membrane Toxicity", Miller, M.W. and Shamoo, A.E., Eds. 67, (Plenum Press, New York, 1977).
22. Mueckler, M., Caruso, C., Baldwin, S.A., Panico, M., Blench, I., Morris, H.R., Allard, W.J., Lienhard, G.E., Lodish, H.F., Science 229, 941 (1985).
23. Elbrink, J. and Bibler, I., Science 188, 117/(1975).
24. Jones M.N. and Nickson, J.K., Biochim. Biophys. Acta 650, 1 (1981).
25. Baldwin, S.A., Baldwin, J.M., Lienhard, G.E., Biochem. 21, 3836 (1982).
26. Owen, J.D. and Solomon, A.K., Biochim. Biophys. Acta 290, 414 (1972).
27. Kalckar, H., Nature 138, 289 (1936).
28. LeFevre, P.G., Pharmacol. Rev. 13, 39 (1961).
29. Stein, W.D., "The Movement of Molecules across Cell Membranes" Ch. 8, (Acad. Press, N.Y., 1967).
30. Batt, E.R. and Schachter, D., J. Clin. Inves. 52, 1686 (1973).
31. Kletzien, R.F., Purdue, J.F., Springer, A., J. Biol. Chem. 247, 2964 (1972).
32. Taverna, R.D. and Langdon, R.G., Biochim. Biophys. Acta 323, 207 (1973).
33. Lin, S. Lin, D.C. Flanagan, M.D., Proc. Natl. Acad. Sci. USA 75, 329 (1978).
34. Baker, G.F. and Widdas, W.F., J. Physiol. (Lond.) 231, 143 (1973).
35. Gorga, F.R. and Lienhard, G.E., Biochem. 20, 3108 (1981).
36. Holman, G.D. and Rees, W.D., Biochim. Biophys. Acta 685, 78 (1982).
37. Kaye, G I., Hoefle, C.M., Fenoglio, F.B., Fischbarg, J., J. Cell Biol. 61, 537 (1974).
38. Wieth, J.0., Dalmark, M., Gunn, R.B., Tosteson, D.C., in "Erythrocytes, Thrombocytes, Leukocytes", Gerlach, E., Moser, K., Deutsch, E., Williams, W., Eds., p. 71, (Verlag, Stuttgart, 1972).
39. Schnell, K.F., Biochim. Biophys. Acta 282, 265 (1972).
40. Hayakawa, M., Acta Soc. Ophthalmol. Jap. 75, 204 (1971).
41. As reviewed by Naftalin, R.J. and Holman, G.D., in "Membrane Transport in Red Cells", Ellory, J.C. and Lew, V.L., Eds., p. 299, (Acad. Press, N.Y., 1977).
42. Crane, R.K., in "Physiological Effects of Food Carbohydrates", Jeanes, A. and Hodge, J., Eds., p. 2, (Am. Chem. Soc., Wash., D.C., 1975).
43. As discussed in Robinson, R.A. and Stokes, R.H., "Electrolyte Solutions", Ch. 1, (Buttterworths, London, 1968).
44. Solomon, A.K., J. Gen. Physiol. 51, 335s (1968).
45. Dainty, J., Adv. in Botanical Res. 1, 135 (1963).
46. Sha'afi, R.I., Rich, G.T., Sidel, V.W., Bossert, W., Solomon, A.K., J. Gen. Physiol. 50, 1377 (1967).
47. Levitt, D.G., Biochim. Biophys. Acta 373, 115 (1974).
48. Sha'afi, R.I. and Gary-Bobo, C.M., Prog. Biophys. Mol. Biol. 26, 103 (1973).
49. Galey, W.R. and Brahm, J., Biocim. Biophys. Acta, 818, 425 (1985).
50. Lehninger, A.L., "Biochemistry" Ch. 2, (Worth, N.Y., 1975).
51. Canham P.B. and Burton, A.C., Circ. Res. 22, 405 (1968).
52. Jay, A.W.L., Biophys. J. 15, 205 (1975); Longuet-Higgins, H.C. and Austin, G., Biophys. J. 6, 217 (1966).
53. As reviewed in "Water Transport in Cells and Tissues", House C.R., p. 165 (E. Arnold, London 1974).

What is claimed is:

1. A method of inhibiting osmotic water flow across mammalian cell membranes which comprises contacting the water channels of the cell membranes with a glucose transport blocker so as to inhibit osmotic water flow across the membranes.

2. A method of claim 1, wherein the glucose transport blocker is selected from the group, consisting of phloridzin, phloretin, diallyldiethylstilbestrol, cytochalasin B, and ethylidene-D-glucose.

3. A method of claim 1, wherein the contacting of the water channels of the cell membranes is effected in vitro.

4. A method of claim 3, wherein the glucose transport blocker is selected from the group consisting of phloridzin, phloretin, diallyldiethylstibestrol, cytochalasin B, and ethylidene-D-glucose.

5. A method of inhibiting osmotic water flow across mammalian cell membranes which comprises contacting the water channels of the cell membranes with digitonin so as to inhibit osmotic water flow across the membranes.

6. A method of claim 5, wherein the contacting of the water channels of the cell membranes is effected in vitro.

7. A method of inhibiting osmotic water flow across mammalian cell membranes which comprises contacting the water channels of the cell membranes with escin so as to inhibit osmotic water flow across the membranes.

8. A method of inhibiting osmotic water flow across corneal endothelium which comprises mounting the tissue in a chamber so as to form two compartments within the chamber, filling the compartments with solutions of different osmolarity, applying a hydrostatic pressure difference across the corneal endothelium to develop a spontaneous fluid transport towards one compartment, including a large osmotic flow by making one said compartment hypertonic, and blocking said osmotic water flow by applying a glucose transport blocker or digitonin to the water channels of the corneal endothelium.

9. A method of claim 8, wherein the glucose transport blocker is selected from the group consisting of phloridzin, phloretin, diallyldiethylstibestrol, cytochalasin B, and ethylidene-D-glucose.

* * * * *